(12) United States Patent
Care

(10) Patent No.: US 8,339,140 B2
(45) Date of Patent: Dec. 25, 2012

(54) SENSOR ARRANGEMENT

(75) Inventor: Ian C. D. Care, Derby (GB)

(73) Assignee: Rolls-Royce PLC, London (GB)

( * ) Notice: Subject to any disclaimer, the term of this patent is extended or adjusted under 35 U.S.C. 154(b) by 371 days.

(21) Appl. No.: 12/747,263

(22) PCT Filed: Nov. 18, 2008

(86) PCT No.: PCT/GB2008/003879
§ 371 (c)(1),
(2), (4) Date: Jun. 10, 2010

(87) PCT Pub. No.: WO2009/077713
PCT Pub. Date: Jun. 25, 2009

(65) Prior Publication Data
US 2010/0259272 A1    Oct. 14, 2010

(30) Foreign Application Priority Data
Dec. 14, 2007    (GB) .................................. 0724336.3

(51) Int. Cl.
*G01R 29/12*    (2006.01)
(52) U.S. Cl. ...................................................... 324/457
(58) Field of Classification Search .................. None
See application file for complete search history.

(56) References Cited

U.S. PATENT DOCUMENTS

| | | |
|---|---|---|
| 6,407,475 B1 | 6/2002 | Care |
| 6,412,339 B1 | 7/2002 | Care |
| 6,836,559 B2 * | 12/2004 | Abdel-Fattah et al. ....... 382/134 |
| 7,161,486 B2 * | 1/2007 | Care ............................. 340/561 |
| 2003/0071628 A1 | 4/2003 | Zank et al. |
| 2005/0025345 A1 | 2/2005 | Ohta et al. |
| 2005/0071647 A1 | 3/2005 | Fujinuma et al. |
| 2006/0139032 A1 | 6/2006 | Kalokitis et al. |

FOREIGN PATENT DOCUMENTS

DE    103 09 873 A1    1/2004
(Continued)

OTHER PUBLICATIONS

Carter et al.; "An Instrumentation System Using Combined Sensing Strategies for Online Mass Flow Rate Measurement and Particle Sizing;" *IEEE Transactions on Instrumentations and Measurement*; Aug. 2005; vol. 54, No. 4; pp. 1433-1437.
International Search Report mailed on Feb. 17, 2009 in corresponding International Application No. PCT/GB2008/003879.
Written Opinion of the International Searching Authority mailed on Feb. 17, 2009 in corresponding International Application No. PCT/GB2008/003879.

(Continued)

*Primary Examiner* — Vinh Nguyen
(74) *Attorney, Agent, or Firm* — Oliff & Berridge, PLC

(57) ABSTRACT

Utilization of electrostatic sensor elements is known in relation to obtaining images from a surface such as that of a patient with regard to anomalies including carcinomas. Electrostatic sensor elements, by their nature, are susceptible to creating spurious results in terms of their location with respect to the surface of the subject to be viewed. By providing a visual camera within an array of electrostatic sensor elements the electrostatic charge distribution image is provided by the camera. The image can be overlaid and married with the visual image in a proportionate ratio. In such circumstances an improved final image is provided with inherent visual references to allow analysis of the combined rich display image. A visual camera such as a CCD is used as it is substantially of the same size as the electrostatic sensor elements.

16 Claims, 3 Drawing Sheets

FOREIGN PATENT DOCUMENTS

| | | |
|---|---|---|
| EP | 0 351 880 A3 | 1/1990 |
| EP | 1 055 833 A2 | 11/2000 |
| EP | 1 055 923 A2 | 11/2000 |
| EP | 1 503 330 A1 | 2/2005 |
| JP | A-2003-44857 | 2/2003 |
| WO | WO 03/050547 A2 | 6/2003 |
| WO | WO 2004/065971 A1 | 8/2004 |

OTHER PUBLICATIONS

British Search Report conducted on Mar. 28, 2008 in corresponding British Patent Application No. GB 0724336.3.

* cited by examiner

SENSOR ARRANGEMENT

The present invention relates to sensor arrangements and more particularly to sensor arrangements which utilise electrostatic imaging.

BACKGROUND

An electrostatic sensor is used to measure electrostatic charge, primarily by measuring the effect, on an electrode, of lines of flux emulating from the charge being measured. The sensing electrode is associated with an earth shield and provides an output which depends on the magnitude of the charge being sensed. More particularly, the sensor output will usually be proportional to the magnitude of the charge in front of the sensing surface of the electrode, measured as a weighted average across the area of the surface. The degree of sensitivity is also related to the area of the sensing surface and the proximity of the earth shield. The field of view to which the surface responds can be modified, for example by modifying the shape of the earth shield or by moving the sensor toward or away from the object of interest. A measurement made by the sensor at a particular point in time will represent the view of the sensor at that point in time. In the case of moving objects, a consequence of such measurements can be used to provide a more complete understanding of the system being observed, but this approach can give rise to problems, particularly with fast moving or quickly changing system. It will be appreciated that electrostatic sensors can be utilised with regard to monitoring machinery such as bearing assemblies for wear or to provide images for medical analysis such as with regard to the skin of a person.

It is known to isolate the earth shield and provide a bias voltage or charge in order to view particular charge masses.

An example of a prior electrostatic sensor is provided in International Patent Application No. PCT/GB2003/005559 in the name of Rolls Royce plc. It will be appreciated that one advantage with regard to electrostatic imaging with respect to locating defects in the skin of a person is that the image produced is not purely of the surface but has some depth. However, as indicated above the nature of electrostatic sensing leads to distortion. Thus the images produced generally have no tracer elements and therefore render it difficult to determine the exact position of features when not viewed in real time. It is known to provide surface images by appropriate photography utilising a camera such as a charge coupled device in order to create a surface image of the defect. However, such surface images require the skill of a practitioner in order to fully interpret the image received. With regard to cancerous defects, it will be understood that it is necessary to remove deleterious tissue but removal of perfectly good tissue should be avoided. It will be appreciated that generally with regard to skin carcinoma the tissue to be removed will be visible and therefore consideration of cosmetic effects has to be taken into account. Ideally, scaring should be minimised subject to removal of all the deleterious tissue.

SUMMARY OF THE INVENTION

In accordance with aspects of the present invention, there is provided a sensor comprising an array of electrostatic sensor elements, each sensor element capable of producing a respective output signal when the sensor is directed to a region of an object being sensed, the output signals being separately available at the sensor output to provide information relating to the electrostatic charge distribution across the region, the sensor characterised in that within the array of sensor elements a visual image camera is provided to provide a visual image to overlap with the spatial distribution of the array of sensor elements to allow matched comparison of the region.

Typically, the visual image is substantially consistent with the spatial distribution of the array of sensor elements.

Generally, the visual image camera is centrally located within the array of sensor elements. Generally, the visual image camera is a charge coupled device.

Possibly, there is provided more than one visual image camera.

Generally, each sensor element is in a fixed spatial distribution relative to each other and/or the visual image camera.

Generally, a lens is provided to consolidate the output signals received from the electrostatic sensor elements and/or visual image signals received from the visual image camera to provide the visual image.

Also in accordance with aspects of the present invention, there is provided a sensor arrangement incorporating a sensor as described above along with a display and an image control, the image control receiving the output signals from each or selected electrostatic sensor elements to define an electrostatic charge distribution image and image signals from the visual image camera to define the visual image, the image control including a mixer to receive the electrostatic charge distribution image and the visual image, either as a full frame or part frame, and the mixer combining the electrostatic charge distribution image and the visual image by proportionate overlay defined by a predetermined relative ratio specified by the image control as a display image sequence for the display.

Typically, the control incorporates an adjuster for the relative ratio to adjust the proportionate overlay.

Also in accordance with aspects of the present invention there is a method of forming an image comprising a sensor having an array of electrostatic sensor elements, each capable of producing a respective output signal when the sensor is directed to a region of an object being sensed, the output signals being separately available at the sensor output to provide information relating to the electrostatic charge distribution across the region and a visual image camera towards an object being sensed, obtaining an electrostatic charge distribution image on the array of electrostatic sensor elements and a visual image from the visual image camera and combining the electrostatic charge distribution image and the visual image in proportionate overlay to provide a display image.

Generally, the sensor elements are located at sensor positions defined by a substantially regular matrix of positions.

It can be convenient for the visual image to show a wider area, particularly where there is little surface marking whilst the electrostatic image is focused on the area of interest. This assists in location and determining boundaries.

Typically, the sensor elements are substantially contiguous across the array to provide a substantially contiguous electrostatic charge distribution image.

Generally, the sensor elements form a substantial planar array. Alternatively, the sensor elements form a non-planar array. Further alternatively, the sensor elements are displaceable in order to provide for relative adjustment to achieve substantial formality to a surface of a pre-determined region of an object to be sensed.

Possibly, the sensor elements are arranged to extend inwardly or outwardly of a sphere.

Generally, each sensor element incorporates a respective charge amplifier.

Generally, the output signals are displayed by an appropriate processor adaptation with an image forming element.

Generally, the output signals are displayed, in use, in a manner which allows each output signal to be separately identified.

Generally, the image means are operable to provide an image having a plurality of pixels. Typically each pixel displays a response to a respective output signal. Generally, the image means has a greater number of pixels than there are sensor elements and at least some pixel outputs are created in reference to a sensor element corresponding with a neighbouring pixel. Generally, the pixels form an array laid out in the same manner as the corresponding sensor elements.

Generally, the display intensity of each pixel is determined by the magnitude or polarity of the charge sensed by a corresponding sensor element. Possibly, the display colour of each pixel is determined, in use, by the polarity or magnitude of the charge sensed by the corresponding sensor element. Possibly, the image means and the array of elements are incorporated within a common structure. Possibly, each sensor element incorporates a display element which provides a pixel of the display image.

Generally, one or more of the electrostatic sensor elements are determined as spatial references. Typically, spatial references can be identified within the visual image in order to facilitate relative overlay.

Generally, the proportionate overlay is consistent for the full frame. Alternatively, the proportionate overlay can be varied for parts or portions of the frame.

Generally, the electrostatic output signals are processed by a dithering technique in order to enhance contouring in the electrostatic charge distribution image provided.

BRIEF DESCRIPTION OF THE DRAWINGS

Aspects of the present invention will now be described by way of example and reference to the accompanying drawings in which:—

DETAILED DESCRIPTION OF THE INVENTION

Figure 1:
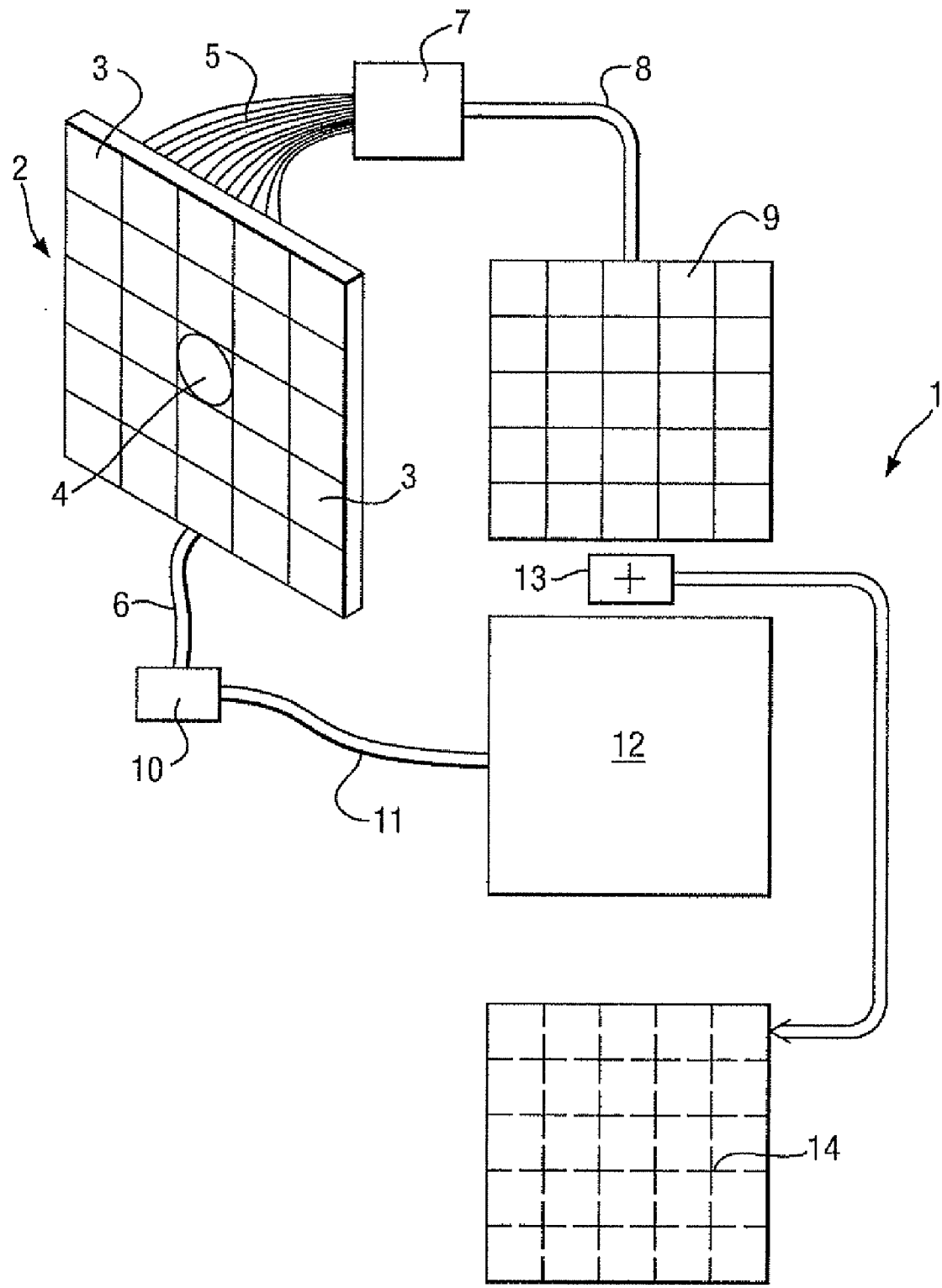
FIG. 1 is a schematic illustration of a sensor arrangement in accordance with aspects of the present invention.

Aspects of the present invention relate to solving problems within a sensor with regard to being able to measure distribution and charge generation along with accurately locate the position of those charges. If the measuring equipment is located too close to the charge source it distorts the measurement. This distortion is an inverse square law. If the measurement equipment is too far away, the resolution of the measurement capability and location is less accurate. It will be appreciated with respect to locating and identifying defects in for instance the skin of a person, the extent of that defect needs to be known accurately, such that all of the infection or otherwise deleterious tissue can be removed or at least monitored but without removing or significantly effecting perfectly good tissue. It will be appreciated that such an approach will provide the best possible patient outcome with the least cosmetic effect, given that many of these skin features are on parts of the body exposed to the sun and therefore visible. In such circumstances tissue removal may cause some sensitivity with regard to cosmetic effects.

As indicated above earlier disclosures such as EP1590676 and other devices utilising electrostatic charge such as disclosed in U.S. Pat. No. 6,407,475, EP1055833, U.S. Pat. No. 6,412,339 and EP1055923 describe utilisation of such electrostatic charges for creation of images. Electrostatic charge distribution images can be useful for analysing surface features whether they be on a person's skin or to determine varying wear conditions in a machine. However, such electrostatic charge distribution images, as indicated, have a degree of sensitivity to position as well as lack of focus and resolution.

In accordance with aspects of the present invention, an electrostatic sensor array is provided in association with an image camera. Thus, typically the electrostatic sensor array has an image camera such as a CCD array camera with a small lens positioned appropriately or at least at a known location within the sensor array. When determining the area to excise, it is the boundary and depth that are important to determine, therefore placing the camera centrally over an area which is likely to be excised it does not detriment the determination of the extent (boundary) of the deleterious tissue. When used for mechanical sensing, such as bearings a different position on matrix 3 may be more appropriate. Such CCD array cameras are known for surveillance and are typically of a similar size or at least acceptable size in comparison with electrostatic sensor elements. In such circumstances, an electrostatic array sensor, similar to that described in EP1590676, can be provided, except at least one of the electrostatic sensor elements is replaced with an image camera, CCD element.

In order to allow appropriate focus and overlap between the electrostatic charge distribution image and the visible image provided by the visible image camera generally a Mylar or similar electrostatic lens is provided in front of the electrostatic sensor element array. The Mylar lens may be of a Fresnel type or made from layered rings of material in order to achieve the desired focussing effects. By such an approach a good visual image from the sensor can be achieved when placed a comfortable distance from the surface of a subject such as a patient. In such circumstances the visual image is coupled with the electrostatic charge distribution image such that a review of the combined images will make it easier to locate electrostatic image features in relation to the patient. Aspects of the present invention provide a method for use in addition to existing clinical examination procedures such as dermatoscopy where the area to be examined is looked at under a magnifying instrument, sometimes with the addition of a facilitating dermatoscopy oil. This dermatoscopy oil as indicated facilitates provision of good visual images and enables holding of the electrostatic charge for improvement in the electrostatic charge distribution image determined by the array of electrostatic sensor elements.

FIG. 1 provides a schematic illustration of a sensor arrangement in accordance with aspects of the present invention. The arrangement 1 comprises an array 2 of electrostatic sensor elements 3 and a visual camera 4 typically with an appropriate lens (not shown). The sensor array 2 has appropriate connections 5, 6 respectively to processors for the electrostatic sensors 3 and the visual camera 4. The connectors 5 through an appropriate multiplexer and control 7 consolidates the output signal responses from the elements 3 and provides through a cable 8, an electrostatic charge distribution image in a display matrix 9. As can be seen generally within the matrix 9 a respective segment is provided correspondingly spatially to the distribution of the sensor elements 3 in the sensor array 2. The visual camera 4 is coupled through the connector 6 to a controller 10, which acts to regulate and control the camera 4 as well as to act as a frame grabber in terms of presenting through signals sent along a cable the visual image 12. The arrangement incorporates a mixer 13 which mixes the electrostatic charge distribution image created by the matrix 9 and the visual image 12. The mixing is achieved by effectively overlaying the images 9, 12 in appropriate relative proportions in order to provide a final or rich display image 14. The matrix 9 and the visual image 12 may exist virtually (eg as a memory store) and not necessarily as a physical display.

In view of the above, visual and electrostatic sensor images are combined and given reference. The rich display image 14 may be more appropriately utilised for observing, monitoring and investigating a subject feature. The subject feature will be interrogated by the array 2 as described above utilising the electrostatic charge distribution image response as well as utilising the visual image provided by the visual camera 4.

By utilising a software dithering technique the electrostatic charge distribution image 9 can be effectively enhanced and contoured to give an electrostatic image that has an effective resolution greater than the size of the array 2. In the embodiment depicted, it will be noted an array, comprising of 5×5 points is depicted. Thus, there will be 24 electrostatic sensor elements 3 and one visual camera element 4. Typically, the camera 4 will be centrally located as depicted, but it is more important that there is overlap between the respective spatial distribution areas of the electrostatic sensor elements 3 and the image area of the camera 4. It will be appreciated that the camera 4 may be arranged to relay larger or similar or exactly the same area as the spatial distribution of the array 4 in order to provide appropriate resolution adjusting effects. It will also be understood that a whole frame, that is to say the whole array 2, may be analysed or only parts or bands of that frame. It is possible through appropriate dithering and interpolation between cells in the array 2, that is to say each sensor element 3 and the corresponding portion of the matrix 9, to give a good approximation to the sensitivity and resolution of a sensor with four times the number of cells. The electrostatic charge distribution image as indicated is superimposed or over-laid with the visual image 12 taken from the visual camera 4. Generally the visual camera 4 is a charge coupled device array appropriately configured and with an appropriate lens to achieve the desired overlap.

The respective image output signals as indicated are combined and mixed in the mixer 13 to give the rich display image 14. In such circumstances it will be appreciated that there is a proportionate overlay of the respective images 9, 12. This proportionate overlay may be fixed but more typically will allow for proportionate adjustment between the respective ratios of the image 9 and image 12. In such circumstances the proportional content of the respective images 9, 12 in the rich image 14 can be adjusted through an appropriate means such as a slider, to effectively fade one image 9 into the other image 12 or vice versa. Provision of a slide proportional relationship will allow an observer such as a clinician observing a defect in the skin of a patient to adjust the rich image 14 until the best or most appropriate mixed image picture is achieved.

Figure 2A:
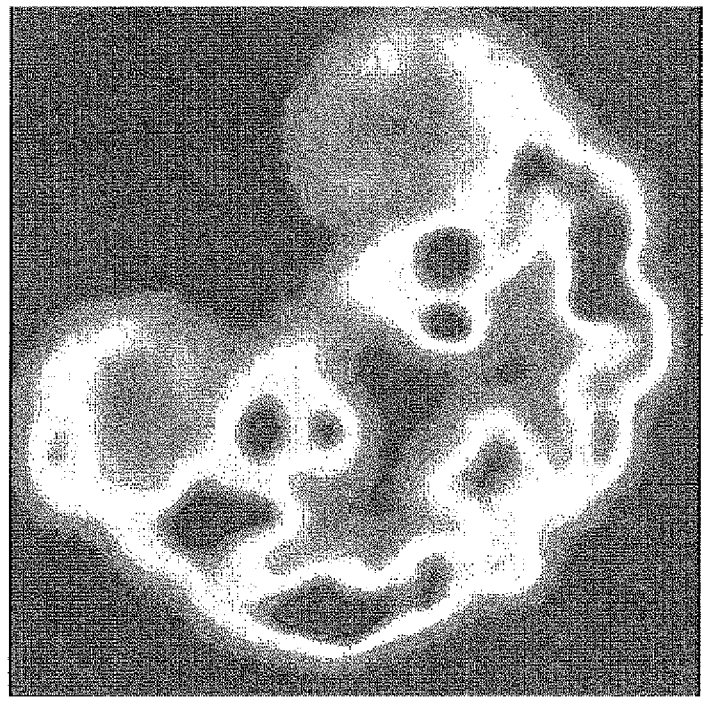
FIG. 2 provides photographic illustrations of images in accordance with aspects of the present invention.
Figure 2B:
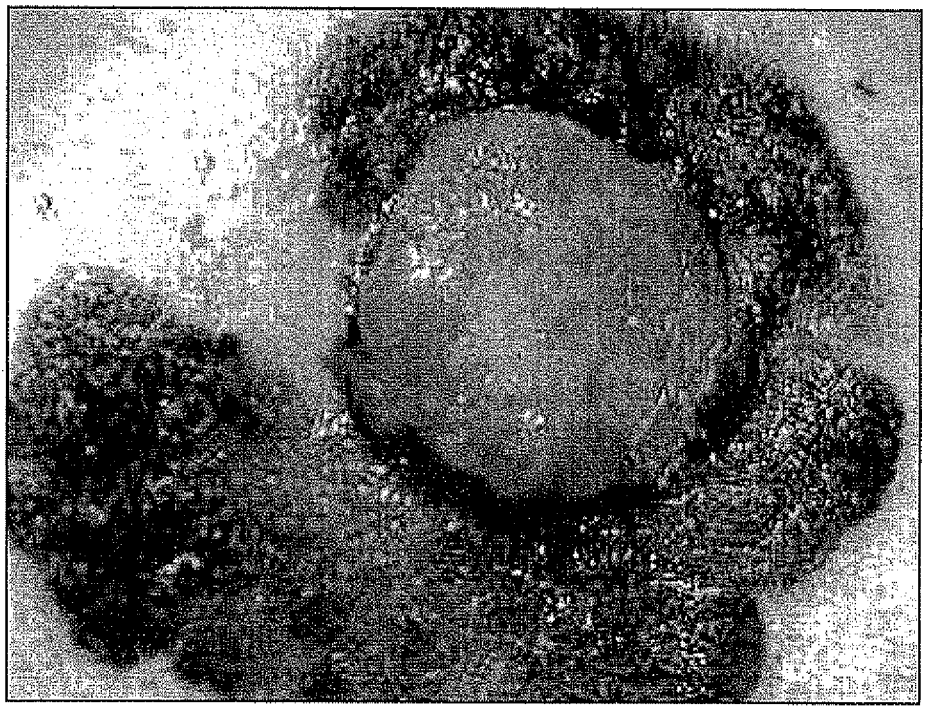

In order to enhance the electrostatic charge image typically a Mylar lens possibly in the form of a fresnel type lens is utilised. Such lenses are well known. Alternatively, electrical lenses such as a control coil and guard ring style lens can be used. In practice the position of the guard ring will tend to go through a critical point beyond which the signal reduces rapidly to the level of the background noise. Care must be taken in order to achieve appropriate operation. As indicated above aspects of the present invention have particular capability with regard to viewing skin discrepancies such as melanoma in a patient. FIG. 2 provides respectively with regard to FIG. 2a an enhanced electrostatic charge distribution image and with regard to FIG. 2b a visual image of a melanoma associated with the electrostatic charge distribution image. Thus, the image provided in FIG. 2a will be achieved through use of a matrix such as that described with regard to FIG. 1 as matrix 9. The visual image provided in FIG. 2b will be presented through the appropriate visual camera as the visual image 12, which will then be combined with the electrostatic charge image as a rich display image 14 (FIG. 1). The images FIG. 2a and FIG. 2b will, in such circumstances, be proportionately superimposed one upon the other to provide a mixed picture which can be adjusted in terms of proportionality between the respective images to allow a viewer, that is to say a clinician to achieve the most appropriate view.

In the above circumstances, under clinical procedures, the clinician may be able to determine the amount of materials being moved more accurately at a first instance. Previously it was known for patients to require more material to be removed in the second operation if the biopsy of the remaining tissue showed some damaged material that is to say cancerous cells, remain. An advantage of aspects of the present invention is that, as indicated, further visual information is provided to ensure adequate removal of deleterious material during the first operation whilst avoiding removal of healthy material.

Figure 3:
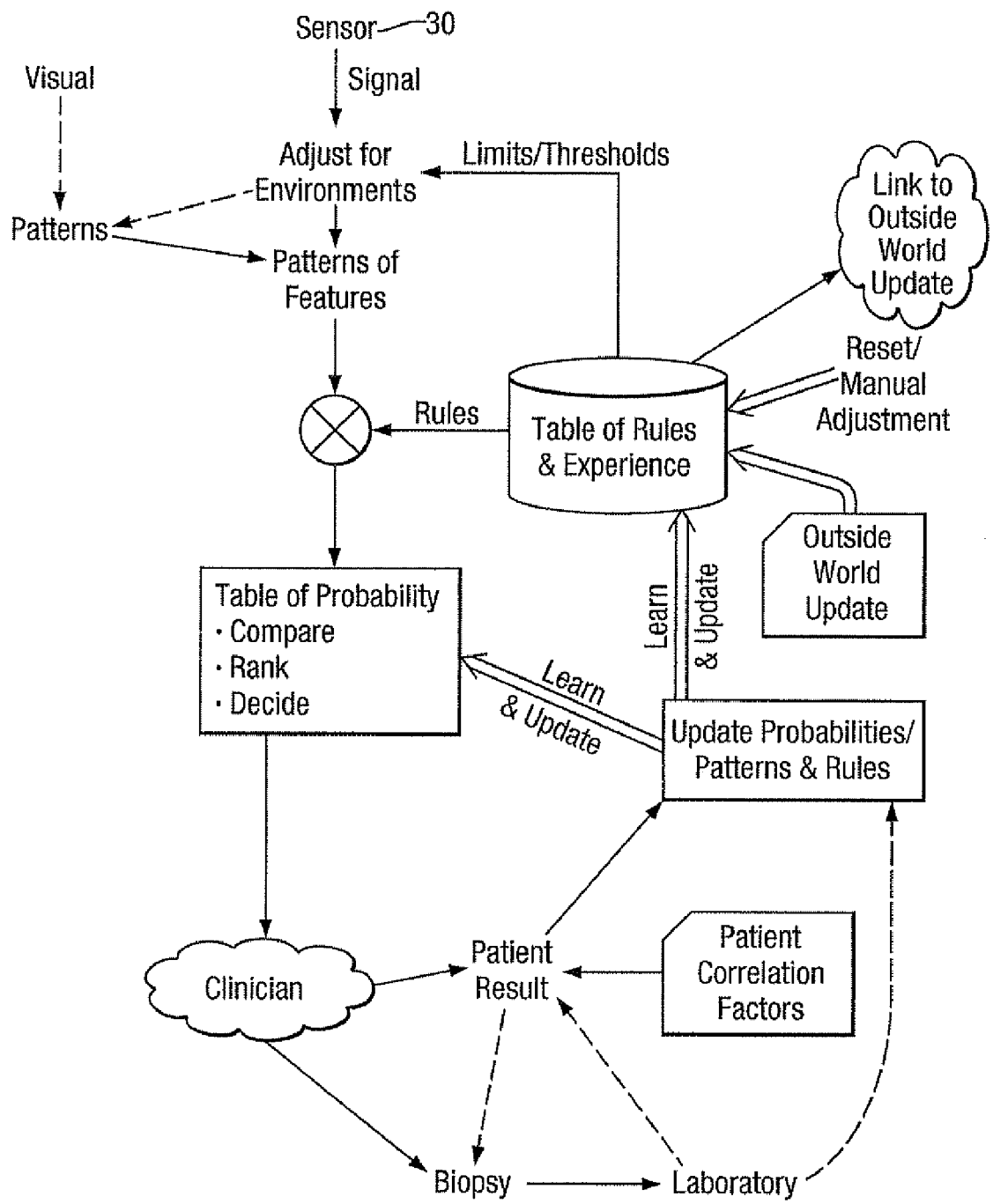
FIG. 3 provides a flow diagram with regard to utilisation of images in accordance with aspects of the present invention in relation to examining images of a patient.

FIG. 3 provides a schematic illustration of analysis and processes with regard to utilisation of the images by a clinician with regard to consideration of surface or skin features. As can be seen the sensor 30, in accordance with aspects of the present invention, provides a signal which will typically be adjusted for environmental conditions to allow for comparison between visual patterns and features by the clinician. The clinician will utilise an existing bank of rules and experience in order to provide information in a directly or through an initial comparison with the rules and then based upon a table of probability, present the image to the clinician for comparison. The clinician will then take a biopsy and provide results through laboratory analysis etc to the patient. Over a period of time it will be appreciated that the images produced in accordance with aspects of the present invention, will enable updating of the probability of identification and the extent of remedial reaction required. This will allow updating of the table of probabilities as well as the rules of experience. The rules of experience can also be updated by external updates from other researchers and results and will allow resetting and adjustment in accordance with other sources of updated such as refinements to the sensor structure and array itself. This will enable the adjustments via environmental controls to also be altered.

Aspects of the present invention provide for a sensor itself, which comprises an array of electrostatic sensor elements 3 in association with a visual camera in order to achieve overlap in the proportional final spatial rich image 14 presented for analysis. Generally, normally in accordance with aspects of the present invention, the sensor array will also be associated with an appropriate display and control to allow proportionate combination of the electrostatic charge distribution image 9 and the visual image 14 in order to achieve appropriate display images. As indicated dynamic real time adjustment in the proportionate overlap between the electrostatic charge distribution image 9 and the spatial image 14 may be beneficial.

Further, in accordance with aspects of the present invention, there is provided a method of providing an image comprising utilisation of a sensor or a sensor arrangement above. The image created by presenting the sensor or sensor arrangement relative to a subject to be viewed, then proportionately combining the electrostatic charge distribution image and the visual image in a ratio determined and possibly variable dependent upon achieving the best performance in terms of potential for evaluation or otherwise.

In view of the above, it will be appreciated that generally a viewer will enable the proportionate overlay between the respective electrostatic charge image and the visual image to be adjusted for best presentation. It will also be understood that appropriate focusing devices will be utilised with regard to the electrostatic sensor elements and/or the visual image in order to again, through appropriate adjustment and tuning, achieve the most appropriate image desirable. The tuning and adjustment of the relative proportionality between the images as indicated with regard to FIG. 3 will allow a sensor and sensor arrangement in accordance with aspects of the present invention to be modified to particular requirements.

Sensors and sensor arrangements in accordance with aspects of the present invention can be used to examine metallic and non-metallic structures including composites, bonded sandwich structures such as nomex, honeycomb cores used in the manufacture of aerospace parts. It may also be possible to provide a sensor in accordance with aspects of the present invention, which can be utilised under water and as indicated above, dermatological oils have been used previously in order to provide enhanced imagery and in accordance with aspects of the present invention, may be utilised in order to facilitate electrostatic image retention.

In addition to above as indicated, portions of the spatial distribution of the electrostatic sensor element can be utilised. The image from the electrostatic charge distribution and the visual image may be compared in real time or frames stored for comparison later. It will be appreciated that appropriate signal conditioning and control can be achieved by storing information for historical comparison. As indicated above, techniques such as dither may also be utilised in order to enhance images provided. Techniques such as edge or boundary detection can be used on both images and marked on the "rich" display.

With regard to electrostatic charge distribution as indicated previously different levels of electrostatic charge may be given different colour values on a scale, for example from red to blue or incrementally. It will be noted that most common colour blindness is red-green so it is advisable to use different pairs of colours. These colours may then be associated, as indicated, proportionately within the visual image. Alternatively, a wash or tint may be provided to the visual image to enhance the colours provided in the electrostatic charge distribution to further enhance the overlay and proportionality of imaging provided. In the above circumstances better representations of carcinomas or bearing wear malfunctions may be achieved.

It will be appreciated that the sensor elements in the array are normally fixed. The array may be planar or non-planar to reflect an object to be viewed or at least a region of that object. Thus, the sensor element may extend inwardly or outwardly in a structure to define the sensor array. The structure may also provide a facility for relative movement between the sensor elements in a spatial distribution. The sensor elements may slide relative to each other to increase or decrease gaps in the spatial distribution are required to alter sensitivity and/or the areas of the region viewed. The visual image can be adjusted to reflect these changes.

Aspects of the present invention relate to image referencing. Thus, within the electrostatic charge distribution image individual sensor elements may be rendered distinctive eg by a noticeable colour or intended flicker. Similarly, the visual image may have a fixed over-mask to provide perspective in the final rich display image formed by overlaying the electrostatic charge distribution image and the visual image. Such references will aid and facilitate interpretation and providing relative context between the electrostatic charge distribution image and the visual image.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A sensor arrangement comprising:
   a sensor; and
   an image control, the sensor comprising an array of electrostatic sensor elements, each sensor element capable of producing a respective output signal when the sensor is directed to a region of an object being sensed, the output signals being separately available at a sensor output to provide information relating to an electrostatic charge distribution across the region, the image control receiving the output signals from each or selected electrostatic sensor elements to define an electrostatic charge distribution image, wherein
   within the array of sensor elements, a visual image camera is provided to provide a visual image, and the image control receives image signals from the visual image camera to define the visual image, the image control including a mixer to receive the electrostatic charge distribution image and the visual image, either as a full frame or a partial frame, and the mixer combining the electrostatic charge distribution image and the visual image by proportionate overlay defined by a predetermined relative ratio specified by the image control.

2. A sensor arrangement as claimed in claim 1 wherein the visual image is substantially consistent with or larger than a spatial distribution of the array of sensor elements.

3. A sensor arrangement as claimed in claim 1 wherein the visual image camera is a charge coupled device.

4. A sensor arrangement as claimed in claim 1 wherein a lens is provided to consolidate the output signals received from the electrostatic sensor elements and/or visual image signals received from the visual image camera to provide the visual image.

5. A sensor arrangement as claimed in claim 4 where the lens is an electrostatic or an electromagnetic lens.

6. A sensor arrangement as claimed in claim 1 wherein at least one of the electrostatic charge distribution image and the visual image are virtual and are held in an electronic memory or a frame store or a serial data stream or a compressed image format.

7. A sensor arrangement as claimed in claim 1 wherein the image control incorporates an adjuster to adjust the predetermined relative ratio to adjust the proportionate overlay.

8. A sensor arrangement as claimed in claim 1 wherein each sensor element incorporates a respective charge amplifier.

9. A sensor arrangement as claimed in claim 1 wherein the output signals are displayed, in use, in a manner that allows each output signal to be separately identified.

10. A sensor arrangement as claimed in claim 1 wherein at least one of a display intensity and a colour is determined by at least one of a magnitude and a polarity of a charge sensed by a corresponding sensor element.

11. A sensor arrangement as claimed in claim 1 wherein the proportionate overlay can be varied for parts or portions of the full frame or the partial frame.

12. A sensor arrangement as claimed in claim 1 wherein the electrostatic output signals are processed by a dithering technique in order to enhance contouring in the electrostatic charge distribution image provided.

13. A sensor arrangement as claimed in claim 1 wherein at least one of the electrostatic and the visual output signals are processed by edge detection techniques in order to enhance boundary identification.

14. A sensor arrangement as claimed in claim 1 wherein an earth shield is isolated and a bias voltage or charge is applied.

15. A sensor arrangement as claimed in claim 14 where the bias voltage or charge can be varied, positive or negative with respect to an electrical earth.

16. A method of forming an image comprising:

providing a sensor having an array of electrostatic sensor elements, each of the electrostatic sensor elements being capable of producing a respective output signal when the sensor is directed to a region of an object being sensed, the output signals being separately available at a sensor output to provide information relating to an electrostatic charge distribution across the region and a visual image camera towards an object being sensed;

obtaining an electrostatic charge distribution image on the array of electrostatic sensor elements and a visual image from the visual image camera; and combining the electrostatic charge distribution image and the visual image in proportionate overlay.

* * * * *